(12) United States Patent
Rossell

(10) Patent No.: US 6,386,871 B1
(45) Date of Patent: May 14, 2002

(54) DEVICE FOR SEALING THE PULP CAVITY IN A DEVITALIZED TOOTH

(76) Inventor: Jordi Rossell, 35a, Route de Burenoz, CH 1092 Belmont-sur-Lausanne (CH)

( * ) Notice: Subject to any disclaimer, the term of this patent is extended or adjusted under 35 U.S.C. 154(b) by 0 days.

(21) Appl. No.: 09/943,573

(22) Filed: Aug. 30, 2001

Related U.S. Application Data

(63) Continuation of application No. PCT/IB99/00402, filed on Mar. 12, 1999.

(51) Int. Cl.⁷ .................................................. A61C 5/02
(52) U.S. Cl. .......................... 433/81; 433/102; 433/224
(58) Field of Search .......................... 433/81, 102, 224, 433/89, 90

(56) References Cited

U.S. PATENT DOCUMENTS 5,046,950 A * 9/1991 Favonio ........................ 433/81
5,074,792 A * 12/1991 Bernadat ..................... 433/220

FOREIGN PATENT DOCUMENTS

| BE | 834 432 | 2/1976 |
| EP | 0 538 200 | 4/1993 |

* cited by examiner

Primary Examiner—Nicholas D. Lucchesi
(74) Attorney, Agent, or Firm—Henderson & Sturm LLP

(57) ABSTRACT

A device for sealing the pulp cavity and root canals of a devitalized tooth, comprising a vacuum pump, a first connecting conduit between this vacuum pump and the pulp cavity, a source of fluid substance for sealing this pulp cavity, a second connecting conduit between the source of fluid substance and the pulp cavity, and structure for closing said second conduit in order to bring the source of fluid sealing substance selectively into communication with the cavity.

32 Claims, 2 Drawing Sheets

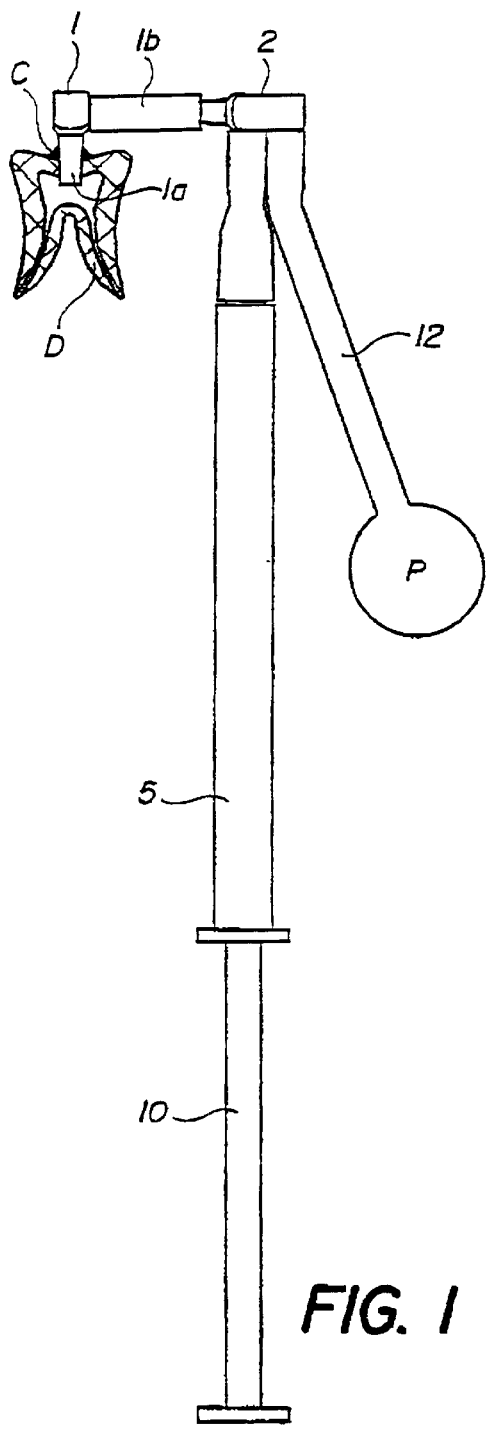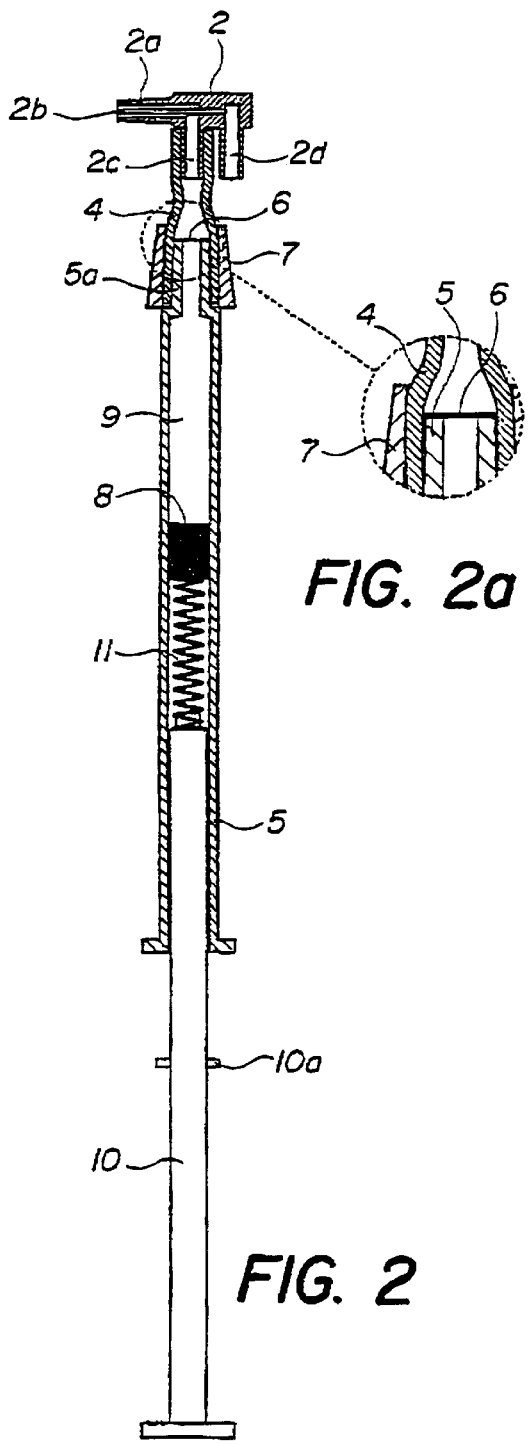
FIG. 1   FIG. 2   FIG. 2a

DEVICE FOR SEALING THE PULP CAVITY IN A DEVITALIZED TOOTH

CROSS REFERENCE TO RELATED APPLICATIONS

This application is a Continuation application of PCT/IB99/00402 filed Mar. 12, 1999, entitled "Device for Sealing the Pulp Cavity in a Devitalized Tooth." Priority is claimed to the PCT application filing date under 35 U.S.C. § 365.

BACKGROUND OF THE INVENTION

1. Field of the Invention

The present invention relates to a device for sealing the pulp cavity and root canals of a devitalized tooth.

2. Description of Related Art

The volume formed by the root system of the tooth is blind because air cannot escape via the apical end of each root. The air therefore escapes as it were via the access formed by the dentist during traditional sealing. Dead volumes may not be filled, presenting both a risk of infection and a weakening of the structure of the tooth.

Filling under vacuum is thus very well suited to sealing the root canals of the teeth after these have been devitalized. The fluid conveyed under vacuum reaches the farthest recesses of the canal geometry, including the entrance of the radial canaliculi on the surface of the walls of each root. The effect of this is to reinforce the structure of the tooth, giving it increased strength.

It has already been proposed to seal devitalized teeth by first applying a high vacuum to the pulp cavity and then connecting this cavity to a source of fluid sealing product, which flows toward this cavity and fills it to the level of the canaliculi by means of the suction created by the vacuum. The first trials carried out by G. Korkhaus and R. Alfter in this field date back to 1958. However, their use was poorly suited to dental techniques and they did not go beyond the experimental stage.

EP 0,299,919 has proposed a method of devitalizing teeth using the phenomenon of cavitation, in which a hypochlorite solution is caused to form bubbles. Once the cleaning and disinfecting have been carried out, the pulp chamber is connected to the vacuum source used to create the cavitation, in order to remove all the liquid by vaporizing it at low pressure. Once the chamber has been dried, a vacuum is established therein and it is then connected to a source of fluid sealing product.

One of the problems associated with this solution lies in the large number of maneuvers needed to move on from the drying stage to the filling stage. Moreover, during the filling stage under vacuum, it is necessary to coordinate the activation of the piston of a syringe, intended to supply the sealing product, with this sealing product being brought into communication with the vacuum pump, which represents a very delicate phase left to the judgment of the operator. If the two actions are not simultaneous, that is to say if the action of the piston is delayed in relation to the sealing product being brought into communication with the underpressure in the cavity to be filled, the flow of the product is slowed down and there is a risk of poor filling of the cavity and especially of the canaliculi.

A proposal for remedying this disadvantage has been set out in U.S. Pat. No. 5,295,828, in which the sealing product is arranged in a reservoir which has an outlet opening for bringing this reservoir into communication with the pulp cavity to be filled, said outlet opening being closed off by a mechanical shutoff element, controlled manually by a lever which allows this shutoff element to be moved away from the outlet opening. The operator opens this shutoff element when the pulp cavity has been placed under vacuum. In this solution, a free piston is mounted in the reservoir in order to equalize the pressure exerted on the fluid sealing product. However, no pressure other than atmospheric pressure is exerted on this piston, so that the cavity is filled only by the suction caused by the underpressure. The communication between the vacuum pump and the pulp cavity is rapidly cut by the sealing product and the underpressure of the pulp cavity is not always sufficient to compensate the losses of head in the supply conduits.

SUMMARY OF THE INVENTION

The present invention relates to a device for sealing the pulp cavity and root canals of a devitalized tooth, comprising a vacuum pump, a first connecting conduit between this vacuum pump and said pulp cavity, a source of fluid substance for sealing this pulp cavity, a second connecting conduit between said source of fluid substance and said pulp cavity, and means for closing said second conduit in order to bring said source of fluid sealing substance selectively into communication with said cavity.

It is an object of the present invention to make it possible to exert simultaneously an underpressure downstream of the reservoir of fluid sealing product and an overpressure upstream thereof, guaranteeing perfect simultaneity of these two effects, in order to promote the filling of the cavity of the lateral canals and the canaliculi by the sealing product.

To this end, the subject of the present invention is a device for sealing the pulp cavity and the root canals of a devitalized tooth.

The overpressure exerted upstream has the main aim of compensating the losses of head in the conduits connecting the reservoir of sealing product and the devitalized pulp cavity. The presence of the calibrated membrane makes it possible to guarantee that the two forces, namely suction downstream and release of the spring upstream, are exerted simultaneously on the sealing product.

BRIEF DESCRIPTION OF THE DRAWINGS

Other advantages will become clear on reading the description and from the drawing accompanying it which illustrates, diagrammatically and by way of example, an embodiment of the sealing device forming the subject of the present invention.

FIG. 1 is an elevation view of this embodiment;

FIG. 2 is a partial view, in cross section, of FIG. 1, with an enlarged detail illustrated by FIG. 2a;

BRIEF DESCRIPTION OF THE INVENTION

Figure 3:
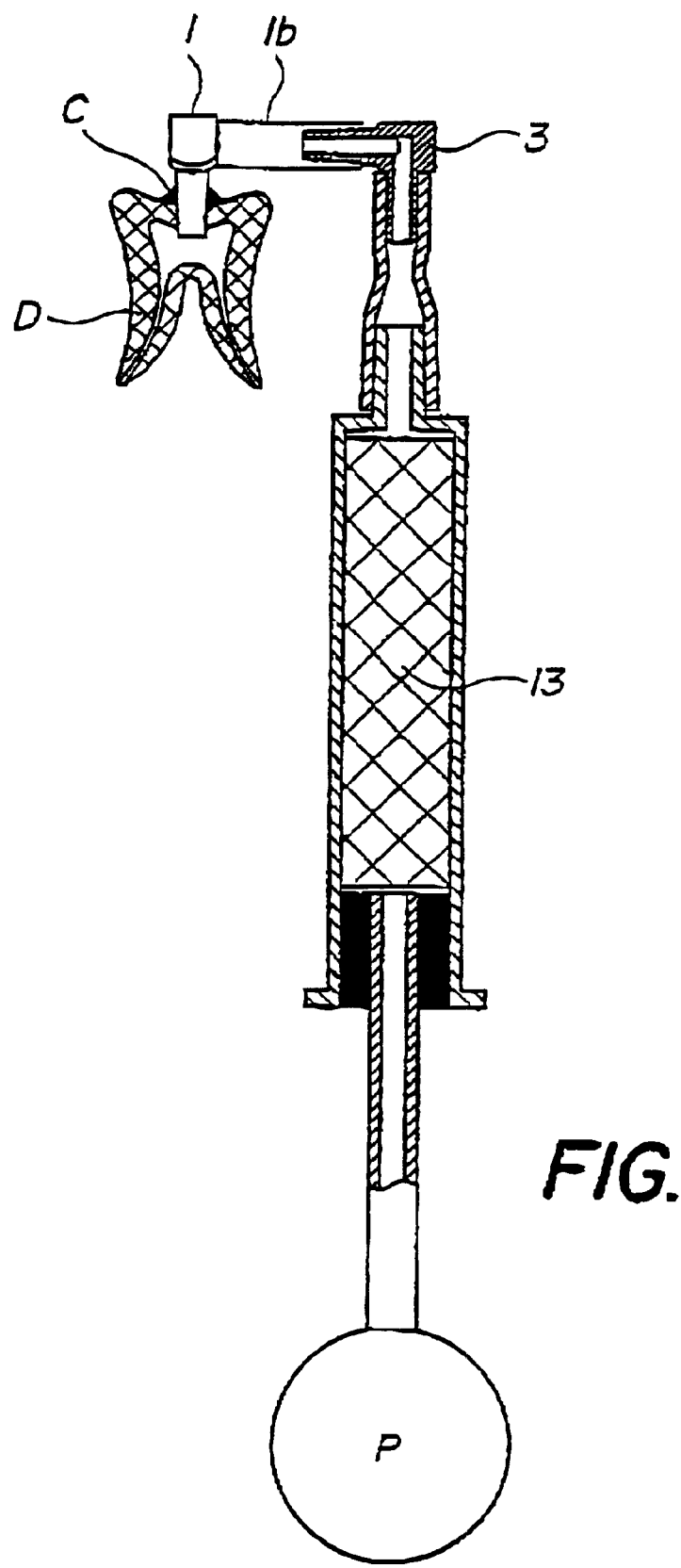
FIG. 3 is a cross-sectional view of a filtering element used during the stage of drying the pulp cavity.

The sealing device illustrated by FIGS. 1 and 2 comprises a first angled endpiece 1, of which one part is formed by a rigid conical conduit 1a which is is formed by a rigid conical conduit 1a which is introduced into the pulp cavity of the devitalized tooth D via an opening formed by the dentist. This conduit 1a is sealed off in a leaktight manner in this opening by means of a cement C, and a photo-polymerizable composite cement also intended to ensure leaktightness. This endpiece 1 comprises a second conduit 1b of PVC. In the case where the tooth D has been devitalized by cavitation, the endpiece 1 can be used both for the devitalization and also for the drying and sealing.

The second conduit 1b of PVC is intended to permit removable and leaktight attachment of a second angled endpiece 2 or of a third angled endpiece 3 illustrated by FIG. 3 and whose role will be explained later.

The second angled endpiece comprises on the one hand two concentric conduits 2a, 2b and on the other hand two conduits 2c, 2d arranged side by side. The conduit 2a communicates with the conduit 2c, and the conduit 2b communicates with the conduit 2d. The conduit 2c is connected via a flexible tubular joining piece 4 to the relatively rigid distribution end 5a of a syringe 5, advantageously of the insulin syringe type. A membrane 6, for example of aluminum, is pinched between the distribution end of the syringe 5 and the tubular joining piece 4. A clamping ring 7 permits a sufficiently firm fixing of the membrane 6.

The inside of the syringe comprises a piston 8 delimiting the space 9 intended to be filled by a fluid product for sealing the pulp cavity of the tooth D. This free piston 8 is connected to the actuating piston 10 of the syringe 5 by way of a coil spring 11. An abutment piece 10a is preferably arranged along the actuating piston 10 of the syringe 5 in order to limit the displacement thereof.

The conduit 2d of the endpiece 2 is connected to a vacuum pump P via a connecting conduit 12. The conduit 2b of the endpiece 2 in communication with the vacuum pump P is formed by a capillary conduit measuring a few tenths of a millimeter in internal diameter, intended to afford considerable resistance to the reflux of the fluid sealing product during the sealing phase, so as to strongly decelerate the flow of this product in the direction of the vacuum pump. It should be noted that this coaxial arrangement of the conduits 2a and 2b makes it possible to form a conduit 2b of the smallest possible cross section while retaining a large annular cross section around it, so as to allow the sealing product to flow with as low a loss of head as possible.

It should be noted that, in addition to the leaktightness which must be ensured between the vacuum pump P and the pulp cavity of the tooth D, the volumes of the conduits must be as small as possible since they enter into the calculation of the residual volume not filled.

The third endpiece 3 (FIG. 3) is intended to replace the endpiece 2 and is fixed in a removable and leaktight manner in the PVC conduit 1b of the endpiece 1. This endpiece 3 is connected to the vacuum pump P by way of a filter 13 during the phase of drying the pulp cavity of the tooth D. This part of the device does not form part, properly speaking, of the present invention and it is also known; it is only shown here in order to explain the sealing process in its entirety.

The drying operation which precedes that of sealing is carried out in two phases, the first being mechanical and the second thermodynamic. The first phase derives from the fact that the residual liquid in the root system includes a proportion of air bubbles, especially subsequent to hydraulic noninstrumental devitalization, in particular by cavitation. These bubbles dilate under the effect of the lowering of the pressure and they instantaneously expel the greater part of the liquid contained in each canal. It is therefore important to proceed with the drying under vacuum immediately after hydraulic cleaning or to recreate an agitation in the canals in order to form smaller dissolved vapor bubbles.

The second phase is the change of state from liquid to vapor of all that remains from the first phase by lowering the pressure below the vaporization threshold. This second endothermic phase takes up to 15 minutes for complete drying of the whole root system and its canaliculi. The disappearance of the vapor flow issuing from the tooth can be measured with a flowmeter on the basis of the pressure difference each side of a restriction or more simply by using a pressure control switch, the vacuum generated by a pump being in inverse relation to its flow rate. The minimum vacuum level supplied by the pump P for proper drying is $10^3$ Pa. At this underpressure, all remaining water ends up being vaporized at body temperature.

Once the desired vacuum level is reached in the cavity to be sealed and the spring 11 is compressed, it suffices advantageously to apply a very slight overpressure on the piston 10 so that, added to the underpressure exerted downstream of the membrane 6 and to the overpressure exerted upstream, this makes it possible to rupture this membrane 6. The calibration of this membrane could also be chosen such that it ruptures by simple addition of the two abovementioned forces without necessitating overpressure. It should be noted that the abutment 10a prevents application of a manual overpressure, the effect of which would be to risk injecting the sealing agent beyond the root system.

Once the membrane 6 has ruptured, the underpressure in the pulp chamber and the pressure of the spring 11 are exerted simultaneously and instantaneously on the sealing product contained in the reservoir 9 of the syringe 5. At the moment when the sealing product reaches the end of the conduit 2b of the endpiece 2, it cuts the connection between the vacuum pump P and the pulp chamber, so that this vacuum pump can be stopped. The root system of the dental cavity can then fill in a time period which depends on the fluidity of the sealing agent.

The residual volume unfilled will in theory be about 1% compared with an atmospheric pressure of $10^5$ Pa. In view of the results observed, it appears that the total volume of the thoroughly drained miniscule radial canaliculi in any event absorbs all or some of this 1%, permitting total filling of the root canals themselves.

The paste/paste, paste/liquid or paste/powder mixture of a two-component sealing material can be used with a consistency which is advantageously very slightly more fluid than that of a sealing mixture for a conventional method. Guttapercha with a low melting point can also be used by heating a syringe filled beforehand with this material. The more fluid the mixture, the more quickly it will reach the whole cavity, but the greater will be the risks of undesirable gas bubbles appearing when it is subjected to the vacuum, and this despite the spring pressure compensation.

Good degassing of the mixture is necessary at a vacuum level at least as great as that at which filling is carried out. This mixture will be introduced into the sealing syringe, taking care to ensure that no bubble is included between the piston and the membrane.

The nature of the membrane 6 will determine the force of rupture as a function of the cross section of the syringe. A conventional aluminum foil disk with a thickness of 5 $\mu$m has given good results with a syringe of 5 mm internal diameter.

The spring 11 used has a length of 18 mm, an external diameter of 3.3 mm and a wire cross section of 0.4 mm. It has given a force of 8.8 N when totally compressed, this force being supported by the membrane 6 subjected downstream to the vacuum on a circular cross section of 4 mm in diameter.

What is claimed is:
1. A device for sealing the pulp cavity and root canals of a devitalized tooth, comprising a vacuum pump, a first connecting conduit between the vacuum pump and said pulp cavity, a source of fluid substance for sealing this pulp cavity, a second connecting conduit between said source of fluid substance and said pulp cavity, and means for closing said second conduit in order to bring said source of fluid sealing substance selectively into communication with cavity, said closing means comprising a membrane calibrated to rupture at a defined pressure.

2. The device as claimed in claim 1, further comprising elastically compressible means and means for pressurizing said elasticaly compressible means for exerting, on the fluid sealing substance in said source, a pressure in the direction of said calibrated membrane, lower than the pressure necessary for rupturing said calibrated membrane.

3. The device as claimed in claim 1 wherein said membrane is calibrated to resist the addition of an underpressure to which said vacuum pump subjects said pulp chamber, exerted downstream of said membrane, and the pressure of said elastically compressible means in the compressed state, exerted upstream of said membrane.

4. The device as claimed in claim 2 wherein said membrane is calibrated to resist the addition of an underpressure to which said vacuum pump subjects said pulp chamber, exerted downstream of said membrane, and the pressure of said elastically compressible means in the compressed state, exerted upstream of said membrane.

5. The device of claim 1 wherein said elastic compression means is formed by a spring arranged between two free pistons.

6. The device of claim 2 wherein said elastic compression means is formed by a spring arranged between two free pistons.

7. The device of claim 3 wherein said elastic compression means is formed by a spring arranged between two free pistons.

8. The device of claim 4 wherein said elastic compression means is formed by a spring arranged between two free pistons.

9. The device of claim 1 further comprising means for limiting the compression of said elastically compressible means.

10. The device of claim 2 further comprising means for limiting the compression of said elastically compressible means.

11. The device of claim 3 further comprising means for limiting the compression of said elastically compressible means.

12. The device of claim 4 further comprising means for limiting the compression of said elastically compressible means.

13. The device of claim 5 further comprising means for limiting the compression of said elastically compressible means.

14. The device of claim 6 further comprising means for limiting the compression of said elastically compressible means.

15. The device of claim 7 further comprising means for limiting the compression of said elastically compressible means.

16. The device of claim 8 further comprising means for limiting the compression of said elastically compressible means.

17. The device of claim 1 wherein said membrane is pinched between a relative rigid conduit and a flexible conduit by an annular clamping element.

18. The device of claim 2 wherein said membrane is pinched between a relative rigid conduit and a flexible conduit by an annular clamping element.

19. The device of claim 3 wherein said membrane is pinched between a relative rigid conduit and a flexible conduit by an annular clamping element.

20. The device of claim 4 wherein said membrane is pinched between a relative rigid conduit and a flexible conduit by an annular clamping element.

21. The device of claim 5 wherein said membrane is pinched between a relative rigid conduit and a flexible conduit by an annular clamping element.

22. The device of claim 6 wherein said membrane is pinched between a relative rigid conduit and a flexible conduit by an annular clamping element.

23. The device of claim 7 wherein said membrane is pinched between a relative rigid conduit and a flexible conduit by an annular clamping element.

24. The device of claim 8 wherein said membrane is pinched between a relative rigid conduit and a flexible conduit by an annular clamping element.

25. The device of claim 9 wherein said membrane is pinched between a relative rigid conduit and a flexible conduit by an annular clamping element.

26. The device of claim 10 wherein said membrane is pinched between a relative rigid conduit and a flexible conduit by an annular clamping element.

27. The device of claim 11 wherein said membrane is pinched between a relative rigid conduit and a flexible conduit by an annular clamping element.

28. The device of claim 12 wherein said membrane is pinched between a relative rigid conduit and a flexible conduit by an annular clamping element.

29. The device of claim 13 wherein said membrane is pinched between a relative rigid conduit and a flexible conduit by an annular clamping element.

30. The device of claim 14 wherein said membrane is pinched between a relative rigid conduit and a flexible conduit by an annular clamping element.

31. The device of claim 15 wherein said membrane is pinched between a relative rigid conduit and a flexible conduit by an annular clamping element.

32. The device of claim 16 wherein said membrane is pinched between a relative rigid conduit and a flexible conduit by an annular clamping element.

* * * * *